(12) United States Patent
Davar

(10) Patent No.: US 7,386,349 B2
(45) Date of Patent: Jun. 10, 2008

(54) RAPID ANALGESIA FOR SKIN PUNCTURE

(75) Inventor: Gudarz Davar, Westlake Village, CA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 736 days.

(21) Appl. No.: 10/859,458

(22) Filed: Jun. 3, 2004

(65) Prior Publication Data

US 2005/0038463 A1 Feb. 17, 2005

Related U.S. Application Data

(60) Provisional application No. 60/476,195, filed on Jun. 6, 2003.

(51) Int. Cl.
*A61N 1/34* (2006.01)
(52) U.S. Cl. .................................................. 607/46
(58) Field of Classification Search .............. 607/46, 607/73
See application file for complete search history.

(56) References Cited

U.S. PATENT DOCUMENTS

| | | | |
|---|---|---|---|
| 3,902,502 A | 9/1975 | Liss et al. ................ | 128/422 |
| 4,147,171 A | 4/1979 | Greene et al. ............. | 128/421 |
| 4,431,002 A | 2/1984 | Maurer et al. ............. | 128/422 |
| 4,989,605 A | 2/1991 | Rossen ...................... | 128/422 |
| 5,052,391 A | 10/1991 | Silberstone et al. ....... | 128/422 |
| 5,069,211 A | 12/1991 | Bartelt et al. ............. | 128/421 |
| 5,109,847 A | 5/1992 | Liss et al. ................ | 128/421 |
| 5,350,414 A | 9/1994 | Kolen ....................... | 607/62 |
| 5,397,338 A | 3/1995 | Grey et al. ................ | 607/115 |
| 5,496,363 A | 3/1996 | Burgio et al. ............. | 607/152 |
| 5,914,704 A | 6/1999 | Yamada et al. ........... | 345/157 |
| 6,023,642 A | 2/2000 | Shealy et al. ............. | 607/74 |
| 6,128,518 A | 10/2000 | Billings et al. ........... | 600/345 |
| 6,445,955 B1 | 9/2002 | Michelson et al. ......... | 607/46 |
| 2004/0015188 A1 | 1/2004 | Coulter ..................... | 607/3 |

*Primary Examiner*—Carl Layno
*Assistant Examiner*—Yun Haeng Lee
(74) *Attorney, Agent, or Firm*—Michael A. Sanzo; Law Office of Michael A. Sanzo, LLC

(57) ABSTRACT

The present invention is directed to a device for providing transcutaneous electrical stimulation (TENS) to the finger of a patient at the same time that the finger is being punctured for the purpose of obtaining a blood sample. The device should reduce the pain associated with this procedure and should be of particular interest to diabetic patients that must perform repeated finger puncture procedures to monitor blood glucose levels.

10 Claims, 3 Drawing Sheets

RAPID ANALGESIA FOR SKIN PUNCTURE

CROSS REFERENCE TO RELATED APPLICATIONS

The present application claims the benefit of U.S. provisional application No. 60/476,195, filed on Jun. 6, 2003, which is incorporated in its entirety herein by reference.

STATEMENT OF GOVERNMENT FUNDING

The United States Government has a paid-up license in this invention and the right in limited circumstances to require the patent owner to license others in reasonable terms as provided for by the terms of NIH Grant No. CA80153 awarded by the Department of Health and Human Services.

FIELD OF THE INVENTION

The present invention is directed to a medical device that can be used to puncture a patient's finger and to methods by which the device is used for obtaining a blood sample. The device reduces the amount of pain experienced by the patient by applying transcutaneous electrical nerve stimulation (TENS) at the same time that the skin of the finger is penetrated. The invention should be of particular benefit to diabetic patients who must regularly monitor blood sugar levels.

BACKGROUND OF THE INVENTION

Approximately 16 million Americans have diabetes and must regularly monitor their blood sugar levels. Kits for assaying blood glucose concentration at home came onto the market approximately 20 years ago and have replaced urine testing as the preferred method for assessing how well a patient's diabetes is being controlled. The kits typically require that a patient puncture a finger with a lancet to obtain a sample for testing. These procedures may be performed several times a day and, due to the high concentration of pain receptors in the fingertips, cause considerable discomfort.

One method of alleviating pain that has been used in other contexts has involved delivering mild pulses of electricity across electrodes taped to a patient's skin (see, e.g., U.S. Pat. No. 4,147,171). The pulses are applied in the region of a patient's body where pain is occurring and appear to interfere with the neuronal transmission of pain signals. The technique has been termed "transcutaneous electrical nerve stimulation" (TENS) and devices for controlling pain using the technique are currently being marketed by several companies, including 3M, American Imex and EMPI. Improvements in TENS technology have generally involved altering the characteristics of the electrical impulses delivered (see, e.g., U.S. Pat. Nos. 4,431,002; 5,109,847; 3,902,50; 5,350, 414; 5,069,211; 4,989,605; and 5,052,391) and in miniaturizing devices to make them more portable or more comfortable for use by patients (see, e.g., U.S. Pat. Nos. 5,397,338; 6,445,955; and 6,023,642). A TENS device that could be conveniently used by diabetic patients to reduce the pain that they experience in monitoring blood sugar levels could significantly improve the quality of life for these patients.

SUMMARY OF THE INVENTION

The present invention is based upon the development of a device specifically designed to alleviate the pain associated with obtaining blood samples by puncturing a patient's finger. Pain sensations are dulled by applying TENS impulses at the same time that the puncture is made. The device is convenient to use and may be employed either in a clinical setting or at home.

In its first aspect, the invention is directed to the device described above. The device includes a stabilization block that will typically be made of metal (e.g., stainless steel) or plastic. The block has a finger opening which is of a size sufficient to permit a patient to insert their finger prior to puncturing. In general, the finger opening will have a diameter of approximately 1.5-3.0 cm. A preferred configuration of the finger opening is as an elongated trough approximately 1-11 cm in length. Mounted on the inner surface of the finger opening are at least two electrodes that are positioned so as to contact a patient's finger when inserted. Preferably, the electrodes are in the form of, or attached to, contact pads made of electrically conductive material, e.g., electrically conductive rubber. It is also preferred that the pads be mounted in such a manner as to compress a patient's finger. For example, one or both of the pads may be spring-loaded or attached to compressible material.

The device also may include standard electrical circuitry that is coupled to the electrodes and capable of delivering pulses of electricity across the electrodes when connected by a patient's finger. Alternatively, the electrical circuitry may be supplied by a separate device such as one of the TENS devices that are presently on the market (see e.g., devices of 3M, American Imex or EMPI). Any of the basic electrical circuits and configurations that have been described in the art for applying TENS impulses may be used in conjunction with the present invention (see, e.g., U.S. Pat. No. 4,431, 002; 4,989,605; 5,052,391; 5,397,338; or 6,445,955). The electrical circuitry should be capable of supplying a minimum of 50 milliamps to the electrodes mounted in the finger opening and should preferably include a regulator for adjusting the intensity and frequency of impulses.

In addition, the stabilization block must have a "lancet opening" that provides access to a patient's finger and permits a puncture to be made. This lancet opening need not necessarily be separate from the finger opening. For example, in the device shown in FIG. 1, the finger opening is a trough which allows a patient's finger to be readily accessed from above.

The stabilization block of the device described above may be mounted on a base unit such as that shown in FIG. 1. The main purpose of the base unit is to provide additional support during the puncture procedure, but it is recognized that the base unit could, if desired, also incorporate other features. For example, some of the electrical circuitry involved in delivering pulses might be associated with the base unit or, the base unit may include an opening which aligns with the finger opening of the stabilization unit and in which a lancet might be mounted. Contact between the stabilization block and the base unit can be maintained by fastening them together using screws, clamps or simply by incorporating a nested design that does not permit the two units to move laterally relative to one another.

In one preferred embodiment, the devices described above include a lancet opening that is separate from the finger opening and which is also located in the stabilization block. The lancet opening connects to the finger opening and provides a passageway through which a lancet mounted in the lancet opening may make contact with a patient's finger. As used herein, the term "lancet" includes any lance, lancet, needle, laser or other device used in the art for performing a skin puncture. Mechanical lancets mounted in the stabilization should generally include means by which they can be mechanically propelled into a patient's finger. For example, the lancet may be spring-loaded and connected to a release that can be activated at the time the TENS impulses are being applied to a patient's finger.

In another aspect, the invention is directed to a method of obtaining a blood sample from a patient by performing a finger puncture with a lancet while concurrently numbing the finger using TENS impulses. Preferably, this method is performed using a device with the characteristics described above.

BRIEF DESCRIPTION OF THE DRAWINGS

FIG. 1 shows one embodiment of a finger puncturing device in both an expanded view (panel A) and an assembled view (panel B). The main elements shown in the drawing are as follows:
1: stabilization block
2: finger opening in the form of an elongated trough
3: left electrode penetrating the stabilization block and terminating on the inner surface of the finger opening
4: electrically conductive contact pad attached to the right electrode
5: screw hole for mounting stabilization block on base unit
6: base unit
7: screw hole for mounting stabilization block
8: right electrode removed from stabilization block; the electrode is spring-loaded to compress a patient's finger when inserted into the finger opening
9: top face of stabilization block (1)
10: front face of stabilization block (1)
12: spring loaded electrode
FIG. 2 shows various views of the stabilization block of FIG. 1 (reference numeral 1). Panel A is a top view and the top face of the stabilization block has been given reference numeral (9). The block in this example is approximately 2.5 inches in length and 2.5 inches in width. Panel B is a front view with the front face of the stabilization block having been given reference numeral (10). The block in this example has a height of about 1.35 inches.

FIG. 3 shows a stabilization block (1) with a spring-loaded electrode (12) on the right side and penetrating the bock. A handle forms part of the electrode and is shown lying outside of the block. A patient could draw back on this to compress the spring and cause the portion of the electrode within the finger opening (2) to withdraw during the time that a finger is inserted into the device. The handle could then be released to compress the finger inside the finger opening. The left side electrode is not spring-loaded and is shown in the figure as reference numeral (3).

DETAILED DESCRIPTION OF THE INVENTION

Figure 1B:
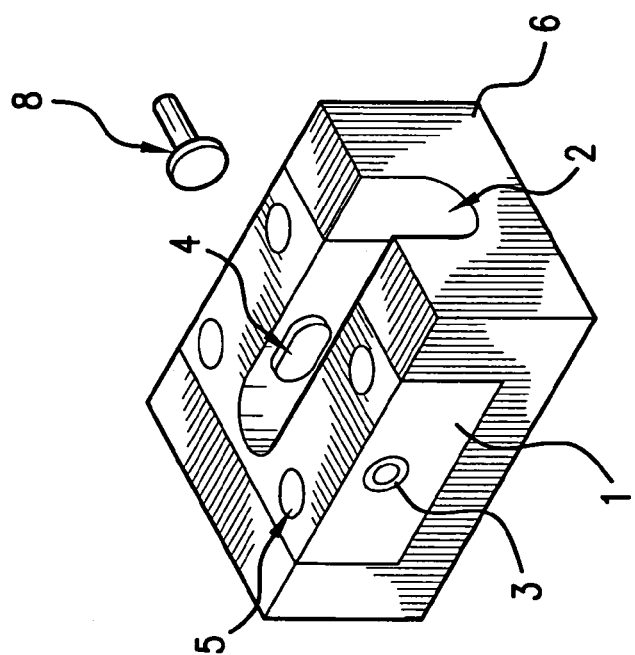
FIG. 1.
Figure 1A:
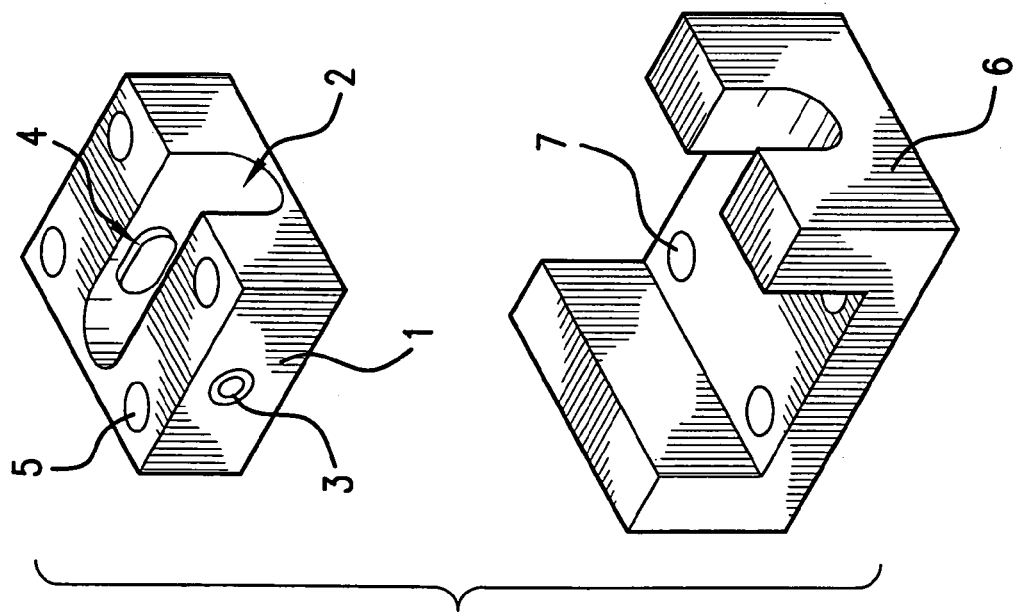
Figure 2A:
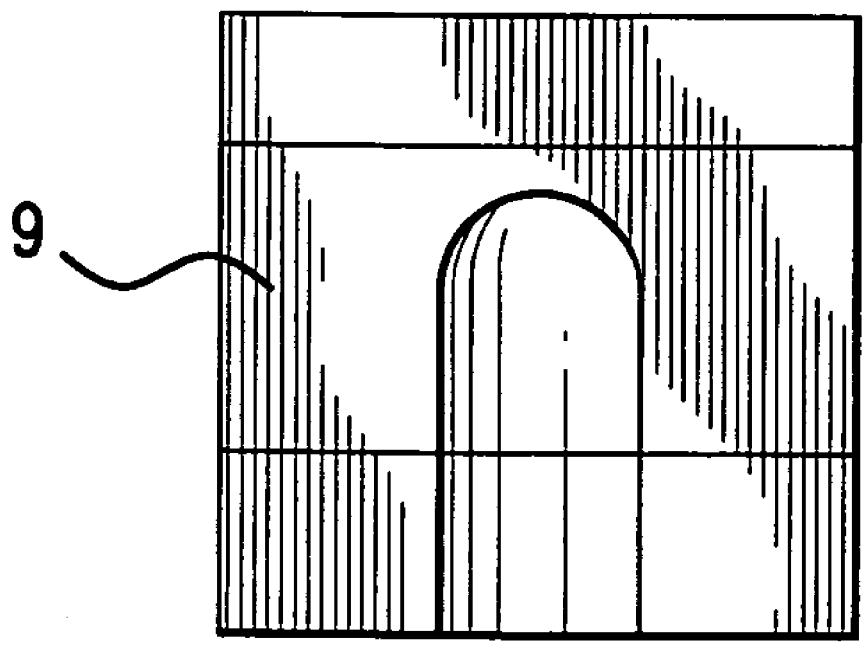
FIG. 2.
Figure 2B:
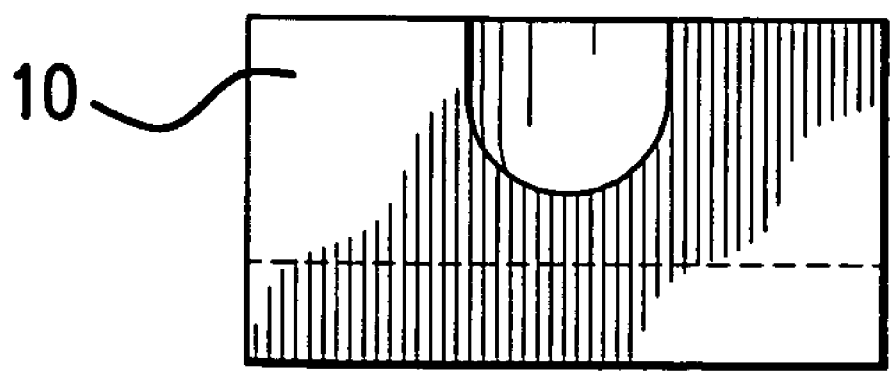
Figure 3:
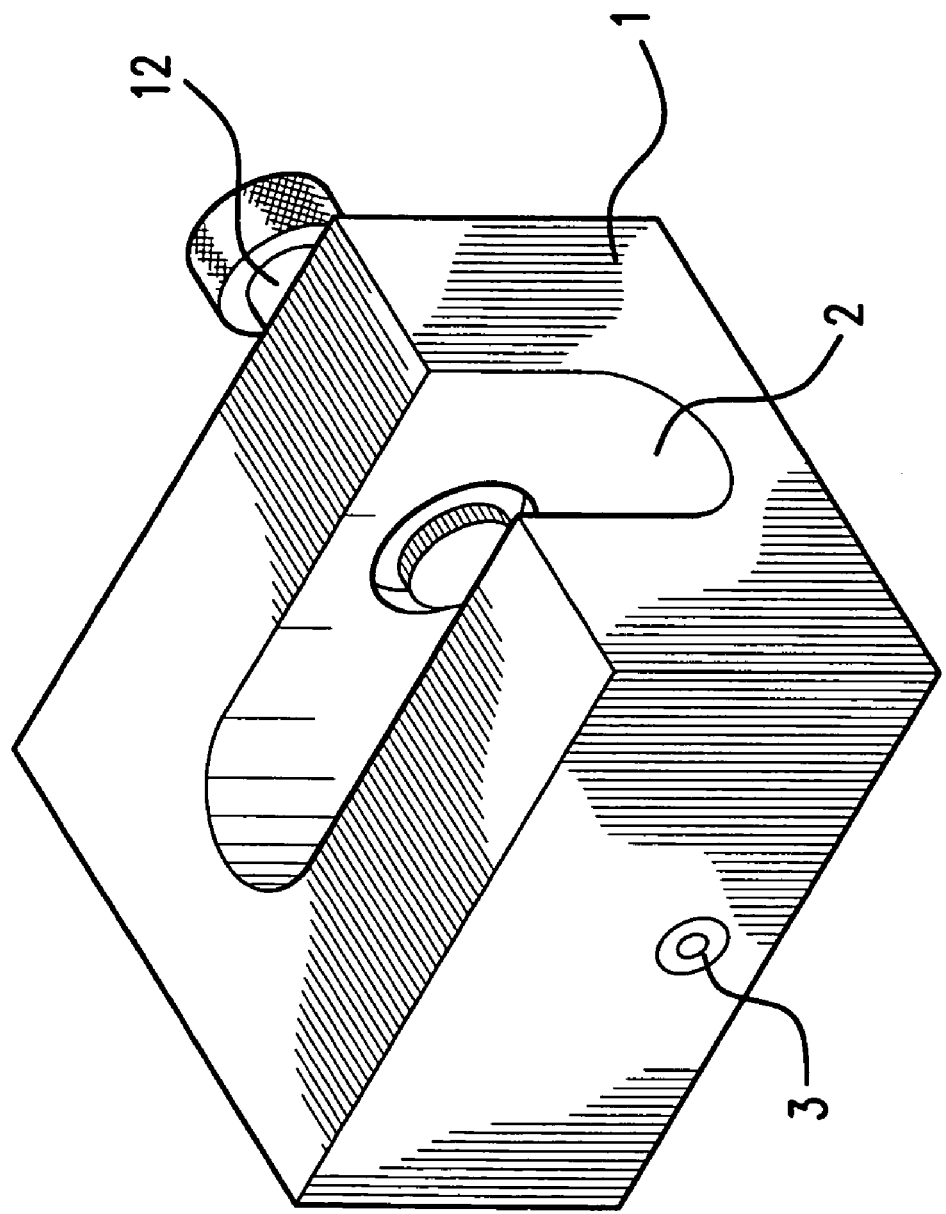
FIG. 3.

The present invention is directed to a device that can be used to apply TENS pulses to a patient's finger during the time at which a blood sample is being taken. Its main components are shown in FIG. 1. The device is made up of a stabilization block (1) that will typically be made of a metal or plastic. The actual dimensions of the block can vary within a wide range of parameters, but typically a device such as that shown in the figure will be roughly 1.5-10 inches in length and width and about 1-3 inches in height. Although we refer herein to a stabilization "block," it is not essential that this take the form of a square as shown in the figure and the term "block" includes rectangles, cylinders and other shapes.

The stabilization block must contain an opening into which a patient's finger may be inserted. In the figure, this is shown in its preferred configuration which is in the form of an elongated trough. The trough must be wide enough to accommodate a patient's finger, roughly 1.5-3.0 cm in width, and long enough to accommodate a sufficient portion of fingertip to contact the electrodes. In general, the length will be between about 1 and 11 cm, with a length of about 3-8 cm being typical.

The stabilization block must include at least two electrodes, preferably mounted on either side of the inner surface of the finger opening. The electrode on the left side of the finger opening is shown in FIG. 1 as reference numeral (3). As shown in the figure, the electrode penetrates through the stabilization block and terminates on the inner surface of the finger opening. Penetrating the block in this way is one convenient way for mounting electrodes. However, other methods can be used equally well, with the only requirement being that the electrode be available for contacting a patient's finger when inserted into the stabilization block. The electrodes preferably end in a stabilization pad (4) which may be spring-loaded (8) in order to compress a patient's finger. The contact pad should be made of material that is capable of transmitting current from the attached electrode to a patient's finger. For example, the contact pad may be made of electrically conductive rubber.

The device may also include a base unit (6) on which the stabilization block can be mounted for further support. In order to secure this stabilization block to the base unit, screws may be inserted in appropriately matched holes (5 and 7). Other methods of maintaining good contact between the stabilization block and the base unit can also be used, such as clamps, bolts or by designing the components in a manner that prevents lateral movement of the stabilization block after mounting The device also includes, or can be connected to, electrical circuitry for delivering TENS impulses across the electrodes and to a patient's finger (not shown in FIG. 1). The circuitry may be either built into the stabilization block or delivered using one or more external components, e.g., those available in commercial TENS devices now on the market. Any of the circuit configurations that have been described in the art are suitable for delivering TENS impulses can be used in conjunction with the present invention. Typically, these include an electrical pulse generator which delivers impulses at a predetermined or selectable frequency and lead wires that attach to electrodes. Preferably, regulators are included for adjusting the intensity of signals and the frequency of pulses. A good TENS system should be capable of delivering 0-70 milliamps at a pulse frequency of roughly 1-100 pulses per second and with a pulse width of 0-400 msec. Examples of circuitry that can be used in the present device may be found in U.S. Pat. Nos. 4,431,002; 4,989,605; 5,052,391; 5,397,338; and 6,445,955, the teachings of which are hereby incorporated by reference.

The stabilization block must include an opening that allows a patient's finger to be punctured by a lancet while TENS pulses are being delivered. This "lancet opening" may be the same as the finger opening or constitute a separate part of the stabilization block. For example, in FIG. 1, the finger opening (2) is in the form of an elongated trough which is open at the top. Thus, a patient would have direct access to a finger placed in a "palms up" position in the device and could puncture the finger's skin using a lancet thrust from above. However, the top portion of the finger trough could also be covered and a separate lancet opening incorporated within the stabilization block above the finger trough. As long as the lancet opening connected to the trough and provided a passageway for delivering the lancet it would be suitable for use in the device. A lancet could also be suspended in the lancet opening and mechanically propelled downward. For example, the lancet could be spring-loaded with a release available for activation after a patient's finger has been inserted into the finger trough.

Using the device involves a patient inserting their finger into the finger opening in a manner that allows it to be compressed by the contact pads. Once inside, TENS impulses are delivered to the finger to a degree sufficient to dull pain sensations. The frequency and amplitude of pulses necessary to achieve such an effect will vary from patient to patient and it is therefore preferable that electrical circuitry allow patients to modulate pulse amplitude, frequency and width. Typically, good results should be obtainable using 5-70 milliamps, a frequency of 50-100 Hz, and a pulse width of 50-200 microseconds. With experience, a patient should be able to select parameters that produce an optimal degree of numbing.

Concurrently with the application of TENS stimulation, the patient's finger is punctured using a lancet, lance, needle or other similar device. Suitable implements are commercially available and procedures for performing finger punctures are well known in the art. The instruments used for penetrating skin should, of course, be sterile, disposable, and the skin being punctured may optionally be treated with an antiseptic agent, such as alcohol, prior to penetration. Spring-loaded lancets may also be used and as noted above, may optionally be suspended within the device. Lancets, including spring loaded lancets, suitable for use in the device are manufactured and sold by many different companies, including Lifescan, Becton Dickinson, Bayer Diagnostics, Owen Mumford, and Roche Diagnostics. The term "lancet" as used herein includes mechanical devices as well as lasers that have been approved for skin penetration, such as those manufactured by Cell Robotics. Although the devices described herein are the most preferred for obtaining blood samples using a finger puncture technique, other devices for applying TENS stimulation can also be used, with the only requirement being that they be adaptable for applying electrical impulses to the finger of a patient.

The devices of the present invention can be used in any setting in which blood samples are obtained from a patient's finger. For example, they can be used in a hospital or physician's office to obtain samples for testing or for drug screening procedures. It is believed that diabetic patients that monitor blood sugar levels at home will benefit most from the use of the devices. These patients often must obtain multiple blood samples in a day and the present devices should make this task considerably more bearable.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A device for puncturing the finger of a patient for the purpose of obtaining a blood sample comprising:
   a) a stabilization block comprising a finger opening of sufficient size to permit the insertion of a patient's finger;
   b) at least two electrodes mounted on the inner surface of said finger opening and positioned so as to contact a patient's finger when inserted into said finger opening; and
   c) a lancet opening in said stabilization block, which may be the same as said finger opening or separate from said finger opening, through which a lancet may pass to puncture a patient's finger when inserted into said finger opening
   d) electrical circuitry coupled to said electrodes wherein said circuitry includes an electric pulse generator capable of delivering pulses of electricity across said electrodes when connected by a patient's finger.

2. The device of claim 1, wherein said electric pulse generator is capable of delivering pulses at a frequency of 1-100 pulses per second.

3. The device of claim 2, wherein said electrical circuitry supplies a minimum of 50 mamps to said electrodes.

4. The device of claim 1, wherein said finger opening has a diameter of 1.5-3.0 cm.

5. The device of any one of claims 1-4, wherein said finger opening has a diameter of 1.5-3.0 cm and is in the form of an elongated trough 1-11 cm in length.

6. The device of claim 5, wherein said electrodes are in the form of, or attached to, contact pads mounted in a manner such that they compress a patient's finger when inserted into said finger opening.

7. The device of claim 6, wherein said contact pads are on opposite sides of said trough.

8. The device of claim 5, further comprising a base unit on which said stabilization block may be mounted.

9. The device of claim 5, further comprising a base unit on which said stabilization block can be mounted.

10. The device of any one of claims 1-4, further comprising a base unit on which said stabilization block can be mounted.

* * * * *